United States Patent
Li et al.

(10) Patent No.: US 11,891,679 B2
(45) Date of Patent: Feb. 6, 2024

(54) HIGH-STRENGTH AND LOW-MODULUS β-TYPE SI-CONTAINING TITANIUM ALLOY, PREPARATION METHOD THEREFOR AND USE THEREOF

(71) Applicant: SOUTH CHINA UNIVERSITY OF TECHNOLOGY, Guangzhou (CN)

(72) Inventors: Yuanyuan Li, Guangzhou (CN); Weiwen Ye, Guangzhou (CN); Chao Yang, Guangzhou (CN); Fen Wang, Guangzhou (CN); Weiwen Zhang, Guangzhou (CN); Zhiyu Xiao, Guangzhou (CN)

(73) Assignee: SOUTH CHINA UNIVERSITY OF TECHNOLOGY, Guangzhou (CN)

( * ) Notice: Subject to any disclaimer, the term of this patent is extended or adjusted under 35 U.S.C. 154(b) by 752 days.

(21) Appl. No.: 16/497,810

(22) PCT Filed: Nov. 15, 2017

(86) PCT No.: PCT/CN2017/111106
§ 371 (c)(1),
(2) Date: Sep. 26, 2019

(87) PCT Pub. No.: WO2018/176853
PCT Pub. Date: Oct. 4, 2018

(65) Prior Publication Data
US 2020/0056267 A1    Feb. 20, 2020

(30) Foreign Application Priority Data
Mar. 27, 2017    (CN) .......................... 201710186636.3

(51) Int. Cl.
C22C 14/00    (2006.01)
A61L 27/06    (2006.01)
(Continued)

(52) U.S. Cl.
CPC .............. *C22C 14/00* (2013.01); *A61L 27/06* (2013.01); *C22C 1/02* (2013.01); *C22C 1/0458* (2013.01);
(Continued)

(58) Field of Classification Search
CPC ................................ C22C 14/00; C22C 30/00
See application file for complete search history.

(56) References Cited

U.S. PATENT DOCUMENTS

2007/0227628 A1    10/2007    Koyanagi et al.

FOREIGN PATENT DOCUMENTS

| CN | 101003873 | 7/2007 |
| CN | 101003873 A * | 7/2007 |

(Continued)

OTHER PUBLICATIONS

Henriques, Vinicius AR, Hugo RZ Sandim, and Cosme Roberto Moreira Silva. "Use of titanium powders obtained by sponge screening and for the HDH process in titanium alloy production for powder metallurgy (P/M)." Materials science forum. vol. 416. Transtec Publications; 1999, 2003. (Year: 2003).*

(Continued)

*Primary Examiner* — Jophy S. Koshy
*Assistant Examiner* — Joshua S Carpenter
(74) *Attorney, Agent, or Firm* — JMB Davis Ben-David

(57) ABSTRACT

A preparation method for high-strength and low-modulus β-type Si-containing titanium alloy involves: preparing an alloy component with, in atomic percentage, 60-70% of Ti, 10-20% of Nb, 5-15% of Zr, 1-10% of Ta and 1-5% of Si and using sponge titanium, sponge zirconium, a tantalum-niobium intermediate alloy and silicon as raw materials, and then uniformly smelting the alloy components to obtain a solidified ingot; then, subjecting the resulting ingot to plastic deformation with a deformation temperature of 800-900° C.

(Continued)

and a deformation rate of 60-80%, and water-quenching same to room temperature; and finally, heating the resulting test sample to a recrystallization temperature, maintaining the temperature for 1-4 h, and carrying out an annealing treatment and air-cooling same to room temperature to obtain the high-strength and low-modulus β-type Si-containing titanium alloy. The resulting titanium alloy is more suitable for use as a medical implant material.

6 Claims, 2 Drawing Sheets

(51) Int. Cl.
    *C22C 1/02*     (2006.01)
    *C22C 1/04*     (2023.01)
    *C22F 1/00*     (2006.01)
    *C22F 1/18*     (2006.01)

(52) U.S. Cl.
    CPC .............. *C22F 1/002* (2013.01); *C22F 1/183* (2013.01); *A61L 2430/02* (2013.01)

(56) References Cited

FOREIGN PATENT DOCUMENTS

| | | | | |
|---|---|---|---|---|
| CN | 101724764 | | 6/2010 | |
| CN | 101760669 | | 6/2010 | |
| CN | 101921929 | | 12/2010 | |
| CN | 103060609 | | 4/2013 | |
| CN | 103320734 | | 9/2013 | |
| CN | 103509959 | | 1/2014 | |
| CN | 103509959 | A * | 1/2014 | |
| CN | 104263996 | | 1/2015 | |
| CN | 103320734 | B * | 2/2015 | |
| CN | 107034383 | | 8/2017 | |
| EP | 1046722 | | 10/2000 | |
| KR | 20090069647 | | 7/2009 | |

OTHER PUBLICATIONS

Espacenet machine translation of CN-101003873-A retrieved on Dec. 3, 2021 (Year: 2007).*

Espacenet machine translation of CN 103509959 A retrieved on Dec. 3, 2021 (Year: 2014).*

Espacenet machine translation of CN 103320734 B retrieved on Dec. 3, 2021 (Year: 2015).*

Deformation and Recrystallization of Titanium and Its Alloys, Heat Treating of Nonferrous Alloys, vol. 4E, ASM Handbook, Edited By George E. Totten, ASM International, 2016, p. 535-545, (Year: 2016).*

B. Cherukuri, R. Srinivasan, S. Tamirisakandala, D.B. Miracle, The influence of trace boron addition on grain growth kinetics of the beta phase in the beta titanium alloy Ti—15Mo—2.6Nb—3Al—0.2Si, Scripta Materialia, vol. 60, Issue 7, 2009, pp. 496-499, ISSN 1359-6462. (Year: 2009).*

* cited by examiner

HIGH-STRENGTH AND LOW-MODULUS β-TYPE SI-CONTAINING TITANIUM ALLOY, PREPARATION METHOD THEREFOR AND USE THEREOF

CROSS-REFERENCE TO RELATED APPLICATIONS

This is the U.S. National Stage of International Patent Application No. PCT/CN2017/111106 filed Nov. 15, 2017, which was published in Chinese under PCT Article 21(2), and which in turn claims the benefit of China Patent Application No. 201710186636.3 filed on Mar. 27, 2017.

TECHNICAL FIELD

The present invention relates to the field of titanium alloy materials, and specifically relates to a high-strength and low-modulus β-type Si-containing titanium alloy, a preparation method therefor and the use thereof.

BACKGROUND OF THE INVENTION

The titanium alloy has the characteristics of a good biocompatibility, excellent comprehensive mechanical properties and good corrosion resistance, and the like. It has become a mainstream material for the development of medical products in the international community. The development of titanium and its alloys can be divided into three eras: the first era is represented by pure titanium and Ti-6Al-4V, which have higher strength and better processing properties. The second era is a new type of α+β-type titanium alloy represented by Ti-5Al-2.5Fe and Ti-6Al-7Nb, which has a more controllable structure and a much improved performance. In the third era, new β-type titanium alloys are most widely studied. These novel β-type titanium alloys, such as Ti13Nb13Zr, Ti-24Nb-4Zr-8Sn, Ti-12Mo-6Zr-2Fe, Ti-35Nb-7Zr-5Ta, Ti-29Nb-4.6Zr-13Ta, Ti—Nb—Zr—Ta—Fe, etc., generally contain elements such as Nb, Zr, Ta, Mo, Sn, Fe, and they have the advantages of high strength, low modulus of elasticity, good corrosion resistance, and good biocompatibility with human body and the like.

For a β-type titanium alloy prepared by the current casting or plastic forming method, the coarse grain size (at least 40 to 60 μm or more) results in lower strength and poor wear resistance. In particular, for medical materials, in addition to superior mechanical properties, fine-grained materials have unique advantages in terms of biocompatibility. Due to a higher grain boundary surface energy, the nanocrystalline/ultrafine crystal material has better osteoclast adhesion and biocompatibility than the same component coarse crystal material. On the other hand, with the development of titanium alloys, there are more and more alloying elements. From the beginning of the binary to the current five elements or more, the purpose is that the new phases formed by the introduction of new elements interact with the traditional titanium alloy phases, which makes the structure of the titanium alloy more diversified, and enables the performance regulation with more space. In particular, the introduction of non-metallic elements can form metal compounds, and the controllability of titanium alloys can be enhanced by regulating the morphology and distribution of metal compounds, which provides many possibilities for preparing titanium alloys with better performance. However, the introduction of non-metallic elements, such as Si, tends to form a weakened phase of a Si containing grain boundary. From the relationship between the microstructure and macroscopic properties of the material and the control mechanism, in general, the continuous thin layer brittleness of the grain boundary plays a weak role in the performance of the material. For example, in the case of slower cooling, the hypereutectoid steel is first transformed into a single-phase austenite, and the pro-eutectoid cementite precipitated in the subsequent cooling process is a continuous network along the austenite grain boundary. The hypereutectoid steel of this structure has a high brittleness and a poor plasticity. How to achieve grain refinement and interrupt the grain boundary continuous phase? Generally, it is impossible to achieve a win-win situation in the above two aspects through heat treatment under normal circumstances.

SUMMARY OF THE INVENTION

In order to solve the above disadvantages and deficiencies of the prior art, it is a primary object of the present invention to provide a preparation method for a high-strength and low-modulus β-type Si-containing titanium alloy.

Another object of the present invention is to provide a high-strength and low-modulus β-type Si-containing titanium alloy prepared by the above preparation method.

A further object of the present invention is to provide a use of the above high-strength and low-modulus β-type Si-containing titanium alloy in a preparation of a biomedical material.

The objects of the invention are achieved by the following technical solutions: A preparation method for a high-strength and low-modulus β-type Si-containing titanium alloy, comprising the steps of:

(1) alloy composition design: preparing an alloy composition with, in atomic percentage, 60-70% of Ti, 10-20% of Nb, 5-15% of Zr, 1-10% of Ta and 1-5% of Si and using sponge titanium, sponge zirconium, a tantalum-niobium intermediate alloy and silicon as raw materials;

(2) casting: uniformly smelting the alloy component prepared in step (1) to obtain a solidified ingot;

(3) high temperature plastic deformation: subjecting the resulting ingot obtained in step (2) to high temperature plastic deformation with a deformation temperature of 800-900° C. and a deformation rate of 60-80%, and water-quenching same to room temperature;

(4) recrystallization: heating the resulting test sample in step (3) to a recrystallization temperature, maintaining the temperature for 1-4 h, and carrying out an annealing treatment and air-cooling same to room temperature to obtain the high-strength and low-modulus β-type Si-containing titanium alloy.

Preferably, the content of the Si element in the step (1) satisfies an as-cast microstructure of the alloy composition to precipitate a Si-containing metal compound (Ti, Zr)$_2$Si (collectively referred to as S2 phase) in a grain boundary and a crystal.

Preferably, the smelting in the step (2) refers to smelting in a vacuum consumable arc melting furnace.

Preferably, the ingot microstructure obtained in the step (2) is characterized by: an acicular S2 phase with a length of 50-100 μm and a spherical S2 phase with a size of 1~3 μm being dispersed in β-Ti grains of 50~300 μm, and a continuous S2 phase is distributed at a grain boundary.

Preferably, the high temperature plastic deformation in the step (3) adopts any one of hot rolling, hot forging, hot extrusion methods and the like.

Preferably, a microstructure characteristic of the plastic deformation after high temperature in step (3) is characterized by: the β-Ti grains being elongated along the deformation direction with appearing a distinct slip band, and the continuous S2 phase distributed at a grain boundary in step (2) being transformed into a lath-shaped S2 phase of 30-60 μm.

Preferably, a microstructure characteristic after the recrystallization in the step (4) is characterized by: a lath-shaped S2 phase of 30~60 μm after high-temperature plastic deformation in step (3) being divided into recrystallized grains of new nucleation into a S2 phase with irregular shape of 5-20 μm.

A high-strength and low-modulus β-type Si-containing titanium alloy is prepared by the above preparation method.

Preferably, a microstructure of the high-strength and low-modulus β-type Si-containing titanium alloy is characterized by an acicular α-Ti phase in an equiaxed β-Ti grain and an S2 phase having an irregular shape, wherein a size of the equiaxed β-Ti grain ranges from 5 to 15 m, a size of the irregularly shaped S2 phase is 5 to 20 m, and a length of the acicular α-Ti phase is 1 to 5 μm.

A use of the above high-strength and low-modulus β-type Si-containing titanium alloy is in a preparation of a biomedical material. Especially, it is used as human implant parts (such as femoral stems, hip bones, knee bones, and so on).

The structure control principle of the high-strength and low-modulus β-type Si-containing titanium alloy according to the present invention is as follows: adding a j-phase stable element such as cerium, zirconium or hafnium into the main element component titanium, further adding a microscale grain refinement element Si with more excellent biocompatibility through the alloy composition design of step (1); obtaining an alloy ingot with continuous S2 phase distributed in the coarse β-Ti grain boundary by the ingot preparation of step (2), and the continuous S2 phase at the grain boundary leading to lower strength and extremely low plasticity of the alloy; in the high temperature plastic deformation of step (3), the β-Ti softening with the Si-containing phase at the high temperature and the more slip phase of bccβ-Ti causing dislocation plugging, delivery, and entanglement, to appear a long strip of slip zone, while the original grain boundary continuous S2 phase being cut by the unsynchronized intergranular slip; in the recrystallization of step (4), the lattice distortion caused by plastic deformation becoming the driving force of recrystallization, and the cellular structure (the cell structure being a microstructure formed by dislocation motion during plastic deformation) becoming the nucleation core of new grains. These high-energy cell structures are flattened at the high temperature, to form sub-crystals, and the subgrains grow into new grains through the subgrain merging mechanism and the subgrain migration mechanism, so that the lath S2 phase of step (3) is divided by the recrystallized grains of the new nucleation, thereby achieving the purpose of strengthening and toughening the material. In summary, the strength and plasticity of the titanium alloy are greatly improved after the recrystallization treatment of the step (4) as compared with the ingot of the step (2). Therefore, the bottleneck problem of the mechanical properties of the continuous grain boundary phase in the material science will be overcome in the present invention.

The preparation method of the invention and the obtained high-strength and low-modulus β-type Si-containing titanium alloy have the following advantages and beneficial effects:

(1) The invention provides a microstructure control method for solving the mechanical properties of the continuous grain boundary phase deteriorated alloy material in the material science based on the composition design of titanium alloy and casting, plastic deformation and heat treatment.

(2) The invention obtains an as-cast structure in which the Si-containing phase is distributed in the coarse β-Ti grain boundary and the dispersed spherical S2 phase is precipitated in the β-Ti crystal grain by the composition design; the spherical dispersed S2 phase interacts with the dislocation to form a fine, diffusely distributed cellular structure that refines the grains after recrystallization. At the same time, the high temperature plastic deformation causes the material to have severe lattice distortion, and the original network boundary precipitates are cut by the incoherence of intergranular slip. The network boundary precipitates are cut to achieve the strengthening and toughening of the material;

(3) The preparation process of the invention is a combination of casting, hot rolling and heat treatment, and the preparation process is relatively mature, so that the parameters of each preparation step can be well controlled. The material properties obtained by multiple preparations are relatively stable, which is favorable for mass production.

DESCRIPTION OF PREFERRED EMBODIMENTS

The present invention will be further described in detail below with reference to the embodiments and drawings, but the embodiments of the present invention are not limited thereto.

A First Embodiment (1) Alloy composition design: the composition of the titanium alloy was designed as 60% of Ti, 20% of Nb, 10% of Zr, 5% of Ta, and 5% of Si in atomic percentage. Sponge titanium, sponge zirconium, a tantalum-niobium intermediate alloy and silicon were used as raw materials to formulate the alloy.

(2) Casting: The casting process is vacuum consumable arc melting. The prepared raw material was pressed into an electrode, wherein the size of the electrode was controlled to be 50 to 70 mm smaller than a crucible and a gap between the electrode and the crucible was controlled between 60 and 80 mm; the smelting speed was 20 μg/min; and the ingot was obtained by twice casting.

(3) High temperature plastic deformation: the ingot obtained by casting was cut into a rectangular parallelepiped sample of 15×25×80 mm. Ti-6Al-4V was selected as the sheath material, and the sheath was assembled with the sample, heated to 900° C., and maintained for 30 min. The hot rolling is multi-pass. Finally, a sample having a rolling ratio of 80% was obtained, and water quenched to room temperature.

(4) Recrystallization: the rolled sample was removed from the sheath and subjected to recrystallization annealing. The sample was placed in a heat treatment furnace, and the temperature was raised to 900° C. with the furnace in a heating rate controlled at 10° C./min, and the temperature was maintained for 4 h, and recrystallization annealing treatment was performed. The annealed sample was taken out to cool to room temperature to obtain a high-strength and low-modulus β-type Si-containing titanium alloy.

Figure 1:
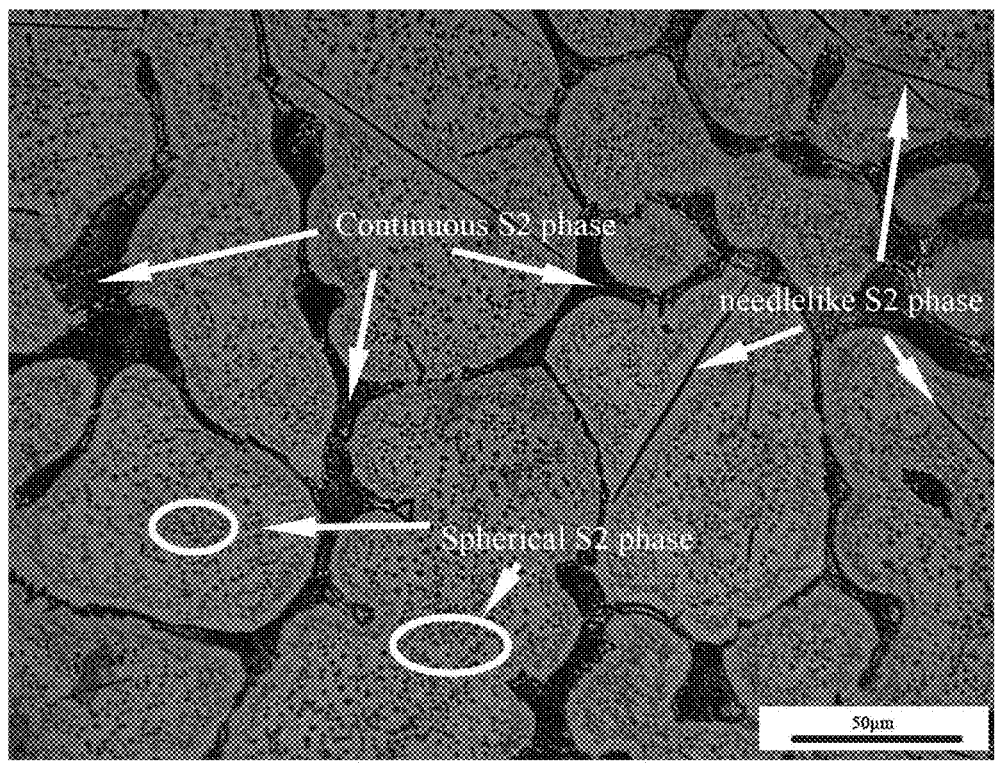
FIG. 1 is a SEM image of the microstructure of the as-cast titanium alloy obtained in the step (2) of a first embodiment.

The SEM image of the microstructure of the as-cast titanium alloy obtained in the step (2) of the present embodiment was shown in FIG. 1. It can be seen from the figure that a spherical S2 phase having a size of about 1 to 3 μm and a acicular S2 phase having a length of about 50 to 100 μm were dispersed on the β-titanium substrate having a microstructure of 50 to 300 μm, and the S2 phase was a continuous S2 phase at the grain boundary.

Figure 2:
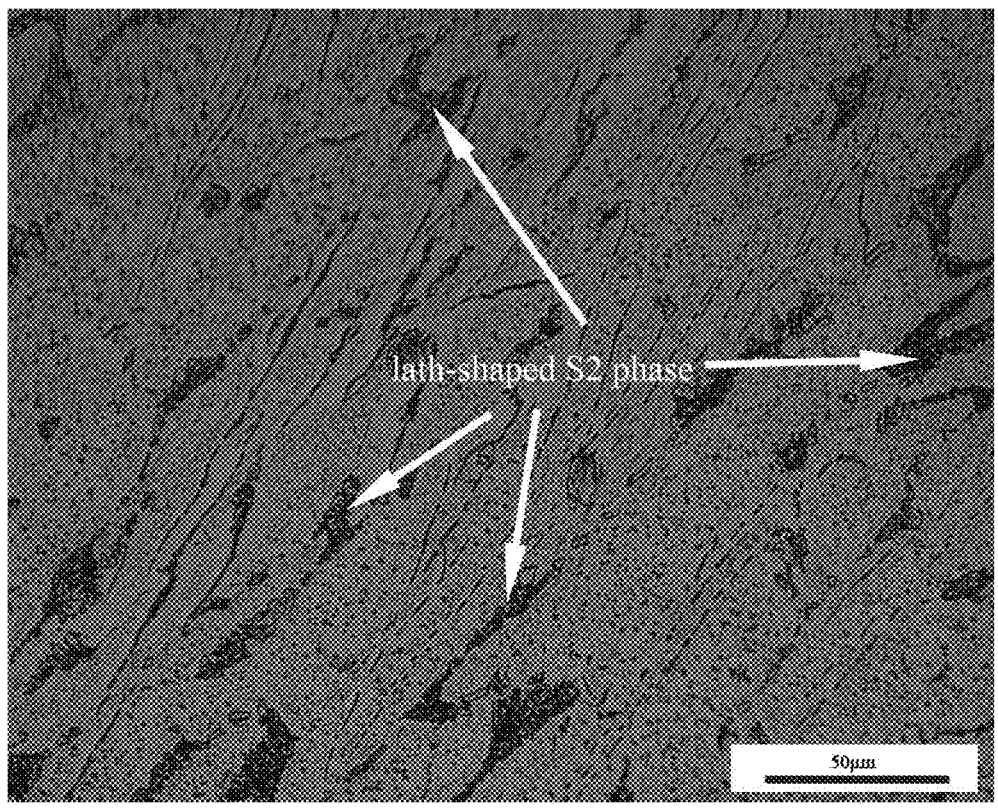
FIG. 2 is a SEM image of the microstructure of the as-rolled titanium alloy after high temperature plastic deformation obtained in the step (3) of the first embodiment.

The SEM image of the microstructure of the as-rolled titanium alloy after the high temperature plastic deformation obtained in the step (3) of the present embodiment was shown in FIG. 2. It can be seen from the figure that after bcc β-Ti was rolled at high temperature, the dislocations were deposited, delivered, and entangled, to occur a long strip of slip. The acicular S2 phase shifted along the rolling direction, and the β-Ti grains decreased from 50~300 μm to 1~2 μm; while the original grain boundary continuous S2 phase were cut by the unsynchronized intergranular slip; in the recrystallization of step (4), the unsynchronized intergranular slip cuts the original S2 phase of the grain boundary, and the continuous S2 phase at the grain boundary in step (2) was transformed into a lath S2 phase with the length of 30~60 μm.

Figure 3:
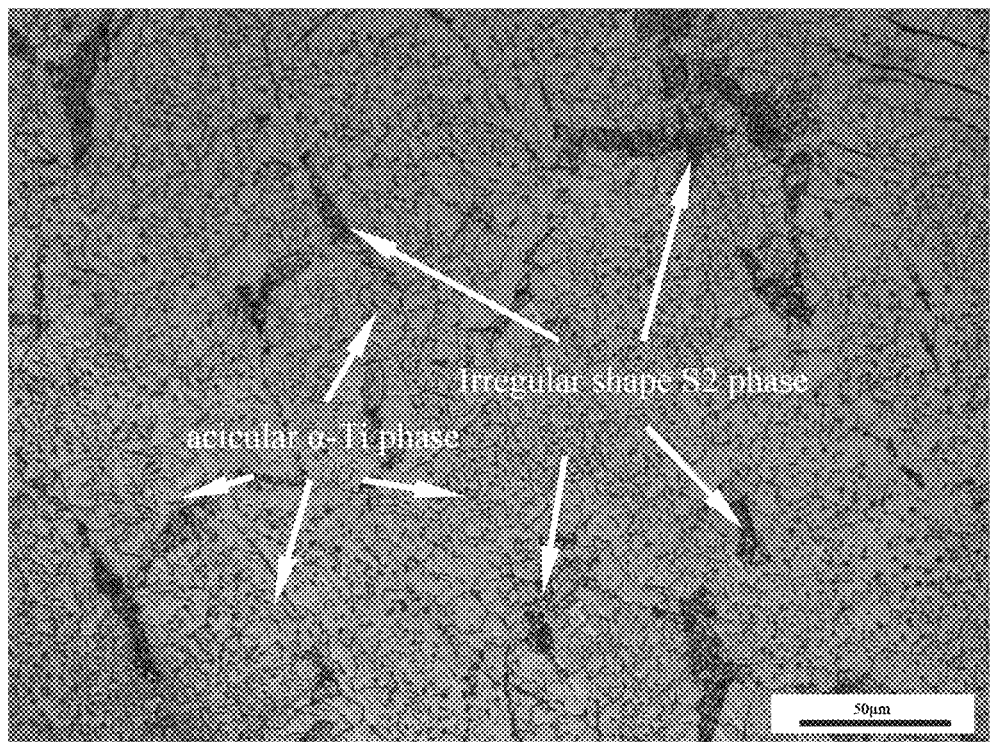
FIG. 3 is a SEM image of the microstructure of the recovered recrystallized titanium alloy obtained in the step (4) of the first embodiment.

The SEM image of the microstructure of the recovered recrystallized titanium alloy obtained in the step (4) of the present embodiment is shown in FIG. 3. It can be seen from the figure that the microstructure was an acicular α-Ti phase in an equiaxed β-Ti grain and an S2 phase having an irregular shape. The size of the equiaxed β-Ti crystal grains was 5 to 15 μm, the size of the irregularly shaped S2 phase was 5 to 20 μm, and the length of the acicular α-Ti phase was about 1 to 5 μm. In particular, after the high temperature plastic deformation of step (3), a lath-shaped S2 phase with a length of 30 to 60 μm was divided into an S2 phase having an irregular shape of 5 to 20 μm by recrystallized grains; while the β-Ti crystal grains are reduced from 50 to 300 μm in the step (2) to 3~4 μm in step (4).

Figure 4:
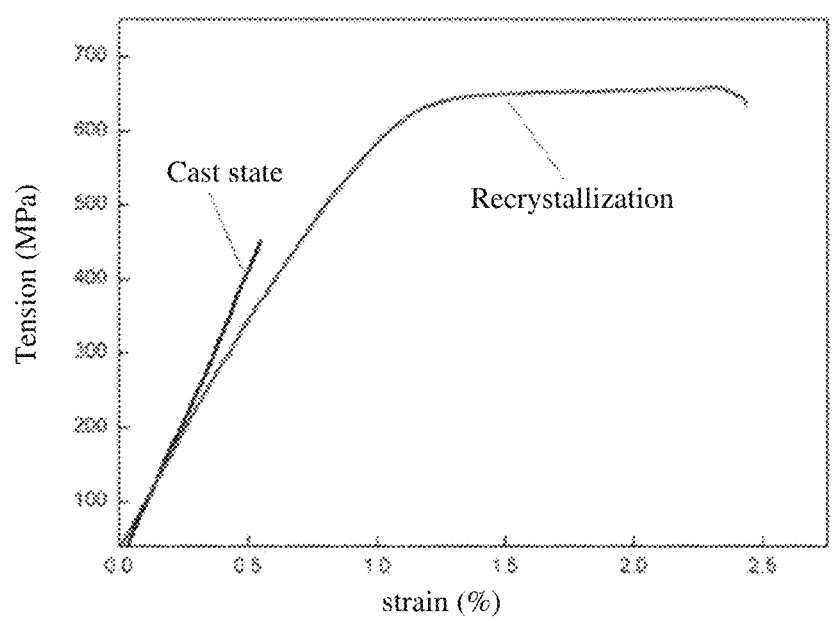
FIG. 4 is a tensile stress-strain curve of the as-cast titanium alloy obtained in the step (2) of the first embodiment and the recovered recrystallized titanium alloy obtained in the step (4).

The tensile stress-strain curves of the as-cast titanium alloy obtained in the step (2) of the first embodiment and the recovered recrystallized titanium alloy obtained in the step (4) were shown in FIG. 4. The results in FIG. 4 showed that the ingot had high brittleness, almost no plasticity, low strength, final breaking strength of 452 MPa, and elastic modulus of 85±1 GPa due to the existence of continuous S2 phase in the grain boundary. The elastic modulus of the recrystallized titanium alloy was 45±2 GPa, which was 40±1 GPa lower than that of the as-cast titanium alloy and was closer to the 30 GPa of the human bone elastic modulus. Meanwhile, the tensile fracture strength of the recrystallized titanium alloy was 658±2 MPa, which was 206±1 MPa higher than cast titanium alloy. In particular, the tensile strain of the recrystallized titanium alloy was as high as 2.4%, which was obviously superior to the non-plastic cast titanium alloy. The resulting β-type titanium alloy had higher strength, greater plasticity, lower modulus of elasticity, and finer grain size, and was significantly more suitable for use as a medical implant material, thus the microstructure control method of the present invention had great advantages.

A Second Embodiment (1) Alloy composition design: the composition of the titanium alloy was designed as 70% of Ti, 10% of Nb, 10% of Zr, 6% of Ta, and 4% of Si in atomic percentage. Sponge titanium, sponge zirconium, a tantalum-niobium intermediate alloy and silicon were used as raw materials to formulate the above ingredients of the alloy.

(2) Casting: The casting process is vacuum consumable arc (VAR) melting. The prepared raw material was pressed into an electrode, wherein the size of the electrode was controlled to be 50 to 70 mm smaller than a crucible and a gap between the electrode and the crucible was controlled between 60 and 80 mm; the smelting speed was 20 μg/min. The ingot was obtained by twice casting. The obtained as-cast microstructure was a spherical S2 phase with a size of about 1~3 μm and a acicular S2 phase with a length of about 50~100 μm dispersed on the dendritic β-titanium matrix of 50~300 μm. The S2 phase was a continuous S2 phase at the grain boundary.

(3) High temperature plastic deformation: the ingot obtained by casting was cut into a cube sample of 50×50×50 mm. The cut sample was heated to 900° C. and remained for 30 min. Constant temperature hot forging was carried out at 900° C. to finally obtain a sample having a forging ratio of 60%, and then the sample was immediately water quenched to room temperature.

(4) Recrystallization: the forged sample was subjected to recrystallization annealing. The sample was placed in a heat treatment furnace, and the temperature was raised to 900° C. with the furnace, in a heating rate controlled at 10° C./min, and the temperature was maintained for 4 h, and recrystallization annealing treatment was performed. The annealed sample was taken out and air-cooled to room temperature to obtain a high-strength and low-modulus β-type Si-containing titanium alloy.

The microstructure of the high-strength and low-modulus β-type Si-containing titanium alloy obtained in this embodiment was an acicular α-Ti phase in an equiaxed β-Ti grain and an S2 phase having an irregular shape. The size of the equiaxed β-Ti grains ranged from 5 to 15 μm, the diameter of the irregularly shaped S2 phase was about 5 to 20 μm, and the length of the acicular α-Ti phase was from 1 to 5 μm. A titanium alloy having properties similar to those of the first embodiment was obtained.

A Third Embodiment (1) Alloy composition design: the composition of the titanium alloy was designed as 65% of Ti, 15% of Nb, 10% of Zr, 7% of Ta, and 3% of Si in atomic percentage. Sponge titanium, sponge zirconium, a tantalum-niobium intermediate alloy and silicon were used as raw materials to formulate the above ingredients of the alloy.

(2) Casting: The casting process is vacuum consumable arc (VAR) melting. The prepared raw material was pressed into an electrode, wherein the size of the electrode was controlled to be 50 to 70 mm smaller than a crucible and a gap between the electrode and the crucible was controlled between 60 and 80 mm; the smelting speed was 20 μg/min. The ingot was obtained by twice casting. The obtained as-cast microstructure was a spherical S2 phase with a size of about 1~3 μm and a acicular S2 phase with a length of about 50-100 μm dispersed on the dendritic β-titanium matrix of 50~300 μm. The S2 phase was a continuous S2 phase at the grain boundary.

(3) High temperature plastic deformation: the ingot obtained by casting was cut into a cylinder sample of Φ15×80 mm. The sample was heated to 900° C. and remained for 30 min. A drawing die with a die hole of 5 mm was selected and pulled at one time, and the drawn sample was immediately quenched to room temperature.

(4) Recrystallization: the drawn sample was subjected to recrystallization annealing. The sample was placed in a heat treatment furnace, and the temperature was raised to 900° C. with the furnace, in a heating rate controlled at 10° C./min, and the temperature was maintained for 4 h, and recrystallization annealing treatment was performed. The annealed sample was taken out and air-cooled to room temperature to obtain a high-strength and low-modulus β-type Si-containing titanium alloy.

The microstructure of the high-strength low-mode β-titanium alloy obtained in this embodiment was an acicular α-Ti phase in an equiaxed β-Ti grain and an S2 phase having an irregular shape. The size of the equiaxed β-Ti grains ranged from 5 to 15 μm, the diameter of the irregularly shaped S2 phase was about 5 to 20 μm, and the length of the acicular α-Ti phase was about 5 μm. The obtained titanium alloy having properties similar to those of the first embodiment was obtained.

A Fourth Embodiment (1) Alloy composition design: the composition of the titanium alloy was designed as 63% of Ti, 17% of Nb, 10% of Zr, 8% of Ta, and 2% of Si in atomic percentage. Sponge titanium, sponge zirconium, a tantalum-niobium intermediate alloy and silicon were used as raw materials to formulate the above ingredients of the alloy.

(2) Casting: The casting process is vacuum consumable arc (VAR) melting. The prepared raw material was pressed into an electrode, wherein the size of the electrode was controlled to be 50 to 70 mm smaller than a crucible and a gap between the electrode and the crucible was controlled between 60 and 80 mm; the smelting speed was 20 μg/min. The ingot was obtained by twice casting. The obtained as-cast microstructure was a spherical S2 phase with a size of about 1~3 μm and a acicular S2 phase with a length of about 50~100 μm dispersed on the dendritic β-titanium matrix of 50~300 μm. The S2 phase was a continuous S2 phase at the grain boundary.

(3) High temperature plastic deformation: the ingot obtained by casting was cut into a cylinder sample of Φ30×30 mm. In order to reduce the damage of the last step of quenching on the upsetting mold, a cold upsetting machine is used for the upsetting system. The size of the cold heading die cavity is 10 mm, the sample is heated to 900° C., kept for 30 minutes, placed in the funnel-shaped pit above the upsetting mold to form the upsetting. After the completion of the upsetting, the sample and the mold were immediately quenched to room temperature.

(4) Recrystallization: the rolled sample was removed from the sheath and subjected to recrystallization annealing. The sample was placed in a heat treatment furnace, and the temperature was raised to 900° C. with the furnace in a heating rate controlled at 10° C./min, and the temperature was maintained for 4 h, and recrystallization annealing treatment was performed. The annealed sample was taken out to cool to room temperature to obtain a high-strength and low-modulus β-type Si-containing titanium alloy.

The microstructure of the high-strength low-mode β-titanium alloy obtained in this embodiment was an acicular α-Ti phase in an equiaxed β-Ti grain and an S2 phase having an irregular shape. The size of the equiaxed β-Ti grains ranged from 5 to 15 μm, the diameter of the irregularly shaped S2 phase was about 5 to 20 μm, and the length of the acicular α-Ti phase was about 5 μm. The obtained titanium alloy having properties similar to those of the first embodiment was obtained.

A Fifth Embodiment (1) Alloy composition design: the composition of the titanium alloy was designed as 67% of Ti, 15% of Nb, 8% of Zr, 9% of Ta, and 1% of Si in atomic percentage. Sponge titanium, sponge zirconium, a tantalum-niobium intermediate alloy and silicon were used as raw materials to formulate the above ingredients of the alloy.

(2) Casting: The casting process is vacuum consumable arc (VAR) melting. The prepared raw material was pressed into an electrode, wherein the size of the electrode was controlled to be 50 to 70 mm smaller than a crucible and a gap between the electrode and the crucible was controlled between 60 and 80 mm; the smelting speed was 20 μg/min. The ingot was obtained by twice casting. The obtained as-cast microstructure was a spherical S2 phase with a size of about 1~3 μm and a acicular S2 phase with a length of about 50-100 μm dispersed on the dendritic β-titanium matrix of 50~300 μm. The S2 phase was a continuous S2 phase at the grain boundary.

(3) High temperature plastic deformation: the ingot obtained by casting was cut into a cube sample of 50×50×50 mm. The cut sample was heated to 900° C. and remained for 30 min. Constant temperature hot forging was carried out at 900° C. to finally obtain a sample having a forging ratio of 70%, and then the sample was immediately water quenched to room temperature.

(4) Recrystallization: the rolled sample was removed from the sheath and subjected to recrystallization annealing. The sample was placed in a heat treatment furnace, and the temperature was raised to 900° C. with the furnace in a heating rate controlled at 10° C./min, and the temperature was maintained for 4 h, and recrystallization annealing treatment was performed. The annealed sample was taken out to cool to room temperature to obtain a high-strength and low-modulus β-type Si-containing titanium alloy.

The microstructure of the high-strength low-mode β-titanium alloy obtained in this embodiment was an acicular α-Ti phase in an equiaxed β-Ti grain and an S2 phase having an irregular shape. The size of the equiaxed β-Ti grains ranged from 5 to 15 μm, the diameter of the irregularly shaped S2 phase was about 5 to 20 μm, and the length of the acicular α-Ti phase was about 5 μm. The obtained titanium alloy having properties similar to those of the first embodiment was obtained.

The above embodiments are preferred embodiments of the present invention, but the embodiments of the present invention are not limited to the above embodiments, and any other changes, modifications, substitutions, combinations, and simplifications made without departing from the spirit and scope of the invention should be equivalent and all of them are included in the scope of protection of the present invention.

The invention claimed is:

1. A preparation method for a β Si-containing titanium alloy, comprising the steps of:
   (1) preparing alloy components with, in atomic percentage, 60-70% of Ti, 10-20% of Nb, 5-15% of Zr, 1-10% of Ta and 1-5% of Si and using sponge titanium, sponge zirconium, a tantalum-niobium alloy and silicon as raw materials;
   (2) smelting the alloy components prepared in step (1) to obtain a solidified ingot;
   (3) subjecting the solidified ingot obtained in step (2) to plastic deformation with a deformation temperature of 800-900° C. and a deformation rate of 60-80%, and water-quenched to room temperature to obtain a plasticly deformed ingot, wherein the plastic deformation in the step (3) adopts any one of hot rolling, hot forging, and hot extrusion;
   (4) heating the plasticly deformed ingot in step (3) to a recrystallization temperature of 900° C., maintaining the recrystallization temperature for 1-4 hr to obtain a recrystallized ingot, and carrying out an annealing treatment and air-cooling on the recrystallized ingot to room temperature to obtain the β Si-containing titanium alloy.

2. The preparation method for the β Si-containing titanium alloy according to claim 1, wherein the smelting in the step (2) refers to smelting in a vacuum consumable arc melting furnace.

3. The preparation method for the R Si-containing titanium alloy according to claim 1, wherein the solidified ingot microstructure obtained in the step (2) is characterized by: an acicular S2 phase with a length of 50-100 μm and a spherical S2 phase with a size of 1~3 μm being dispersed in β-Ti grains of 50~300 μm, and a continuous S2 phase is distributed at a grain boundary.

4. The preparation method for the β Si-containing titanium alloy according to claim 1, wherein a microstructure characteristic of the β Si-containing titanium alloy after the step (4) is characterized by: a lath-shaped S2 phase of 30~60 μm after high-temperature plastic deformation in step (3) being divided into recrystallized grains of new nucleation into a S2 phase with irregular shape of 5-20 μm.

5. A Si-containing titanium alloy prepared by the preparation method according to claim 1, comprising an irregularly shaped S2 phase with a size of 5 to 20 μm.

6. The β Si-containing titanium alloy according to claim 5, wherein a microstructure of the β Si-containing titanium alloy is characterized by an acicular α-Ti phase in an equiaxed β-Ti grain and an S2 phase having an irregular shape, wherein, a size of the equiaxed β-Ti grain ranges from 5 to 15 μm, and a length of the acicular α-Ti phase is 1 to 5 μm.

\* \* \* \* \*